US00PP12704P2

(12) United States Plant Patent
Vandenberg

(10) Patent No.: US PP12,704 P2
(45) Date of Patent: Jun. 18, 2002

(54) CHRYSANTHEMUM PLANT NAMED 'REDBRONZE PILAR'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/756,363

(22) Filed: Jan. 9, 2001

(51) Int. Cl.[7] ..... A01H 5/00
(52) U.S. Cl. ..... Plt./298
(58) Field of Search ..... Plt./286, 296, 298

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4):138–142.*

Broertjes, et al., 1980, "A mutant of a mutant of a . . . Irradiation of progressive radiation induced mutants in a mutation breeding programme with *Chrysanthemum morifolium*", Euphytica, 29:525–530.*

Gosling, ed., 1979, "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods in the Improvement of Vegetatively Propagated Crops", Elsevier Sci Pub. Co., New York, pp. 162–175.*

Searle, et al., 1968, "Chrysanthemums the Year Round", Blanford Press, London, pp. 27–29, 320–327.*

Chan, 1966, "Chrysanthemum and rose mutations induced by x–rays", Am. Soc. Hort. Sci. Proc., pp. 613–620.*

Broertjes, 1966, "Mutation breeding of chrysanthemums", Euphytica, 15:156–162.*

Dowrick, et al., 1966, "The induction of mutations in Chrysanthemum using X– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Redbronze Pilar', characterized by its anemone-type inflorescences that are about 6.3 cm in diameter and with large anemone centers; attractive dark red ray florets and yellow disc florets; freely and early flowering habit; dark green foliage; thick and strong stems; long peduncles and good postproduction longevity with inflorescences maintaining good substance and color for about three or four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Redbronze Pilar'.

The new Chrysanthemum is a product of a mutation induction breeding program conducted by the Inventor in Alva, Fla. The objective of the program is to create new Chrysanthemum cultivars with desirable inflorescence form and floret colors, good substance, and good postproduction longevity.

The new Chrysanthemum is a naturally-occurring whole plant mutation of a proprietary induced mutation that originated by exposing unrooted cuttings of the Chrysanthemum cultivar Bronze Pilar, disclosed in U.S. Plant Pat. No. 10,760, to X-ray radiation. The new Chrysanthemum was discovered and selected by the Inventor as a single flowering plant within a population of plants of the irradiated selection in December, 1997 in Alva, Fla. The selection of this plant was based on its desirable inflorescence form and floret colors and good postproduction longevity.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Redbronze Pilar has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Redbronze Pilar'. These characteristics in combination distinguish 'Redbronze Pilar' as a new and distinct cultivar:

1. Anemone-type inflorescences that are about 6.3 cm in diameter and with large anemone centers.
2. Attractive dark red ray florets and yellow disc florets.
3. Very freely flowering habit with numerous inflorescences per stem.
4. Early flowering, response time is about 49 days.
5. Dark green foliage.
6. Thick and strong stems.
7. Long peduncles.
8. Good postproduction longevity with inflorescences maintaining good substance and color for about three or four weeks in an interior environment.

Plants of the new Chrysanthemum differ from plants of the cultivar Bronze Pilar, primarily in ray floret color as plants of the cultivar Bronze Pilar have bronze-colored ray florets.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Redbronze Pilar' grown as a spray-type cut Chrysanthemum.

The photograph on the second sheet comprises a close-up view of typical inflorescences of 'Redbronze Pilar'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on May 30, 2000 and received 20 long day/short nights followed by short day/long nights until flowering. Plants were grown as single-stem cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Aug. 21, 2000.

Botanical classification: *Chrysanthemum×morifolium* cultivar Redbronze Pilar.

Commercial classification: Anemone spray-type cut Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to rooting.*—About seven to ten days with soil temperatures of 21° C.

*Root description.*—Fine, fibrous and well-branched.

Plant description:

*Appearance.*—Herbaceous anemone spray-type cut flower.

*Flowering stem description.*—Aspect: Erect. Strength: Strong. Length: About 99 cm. Diameter: About 8 mm. Internode length: About 4.3 cm. Texture: Pubescent; fine, white. Color: 146A.

*Foliage description.*—Arrangement: Alternate. Length: About 10.7 cm. Width: About 7.8 cm. Apex: Mostly cuspidate. Base: Mostly truncate. Margin: Plamately lobed; sinuses convergent to overlapping. Texture: Upper and lower surfaces pubescent. Veins prominent on lower surface. Color: Young foliage upper surface: Much darker than 147A. Young foliage lower surface: Close to 147B. Mature foliage upper surface: Darker than 147A; venation, 147A to 147B. Mature foliage lower surface: Close to 147B; venation, close to 146B to 147C. Petiole: Length: About 2.3 cm. Diameter: About 3.5 cm. Color: Upper surface: 147A to 147B. Lower surface: 147B to 147C.

Flowering description:

*Appearance:*— Anemone spray-type inflorescence form with elongated oblong-shaped ray florets. Inflorescences borne on terminals, arising from leaf axils. Disc and ray florets arranged acropetally on a capitulum.

*Flowering response.*—Under natural conditons, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 49 days later.

*Postproduction longevity.*—In an interior environment, flowering stems will maintain good color and substance for about three or four weeks in an interior environment after one week of cool storage.

*Quantity of inflorescences.*—Freely flowering with about 15 inflorescences per flowering stem.

*Inflorescence size.*—Diameter: About 6.3 cm. Depth (height): About 1.9 cm. Diameter of disc: About 3.6 cm. Diameter of receptacle: About 8 mm.

*Ray florets.*—Shape: Elongated oblong. Length: About 3.1 cm. Width: About 9 mm. Corolla tube length: About 6 mm. Corolla tube diameter: About 1.5 mm. Apex: Rounded, acute or emarginate. Base: Attenuate. Margin: Entire. Texture: Satiny, smooth, glabrous; longitudinally ridged. Aspect: Concave to flat. Aspect: Initially upright; when mature, about 90° from vertical. Number of ray florets per inflorescence: About 77 arranged in about four rows. Color: When opening, upper surface: Close to 183A with overtones of 184A. When opening, lower surface: Ground color, 9D, underlain with 183C. Mature, upper surface: Close to 183A to 183B with overtones of 184A; fading to 183C to 184A with subsequent development. Mature, lower surface: Ground color, 9D, faintly underlain with 183C.

*Disc florets.*—Shape: Enlarged tubular; flared at apex. Length: About 1.7 cm. Width: Apex: About 5 mm. Base: About 1 mm. Number of disc florets per inflorescence: Numerous, typically about 171. Color: Immature: 144A to 145A to 154A. Mature, throat: Close to 9A overlain with 183A. Mature, tube: Apex: 9A underlain with 183B. Mid-section: 9A. Base: Close to 155D.

*Peduncle.*—Aspect: Angled about 35 to 40° from vertical. Strength: Strong, flexible. Length: First peduncle: About 11.5 cm. Fourth peduncle: About 14.5 cm. Seventh peduncle: About 18 cm. Diameter: About 3 mm. Texture: Very fine pubescence. Color: 146A.

*Reproductive organs.*—Androecium: Present on disc florets only. Anther color: 9A. Amount of pollen: None observed. Gynoecium: Present on both ray and disc florets.

*Seed.*—Seed production has not been observed.

Disease resistance: Resistance to pathogens common to Chrysanthemum has not been observed on plants grown under commercial conditions.

Temperature tolerance: Plants of the new Chrysanthemum have demonstrated good tolerance to night temperatures as low as 5° C. and day temperatures lower than 40° C.

It is claimed:

1. A new and distinct cultivar of Chrysanthemums plant named 'Redbronze Pilar', as illustrated and described.

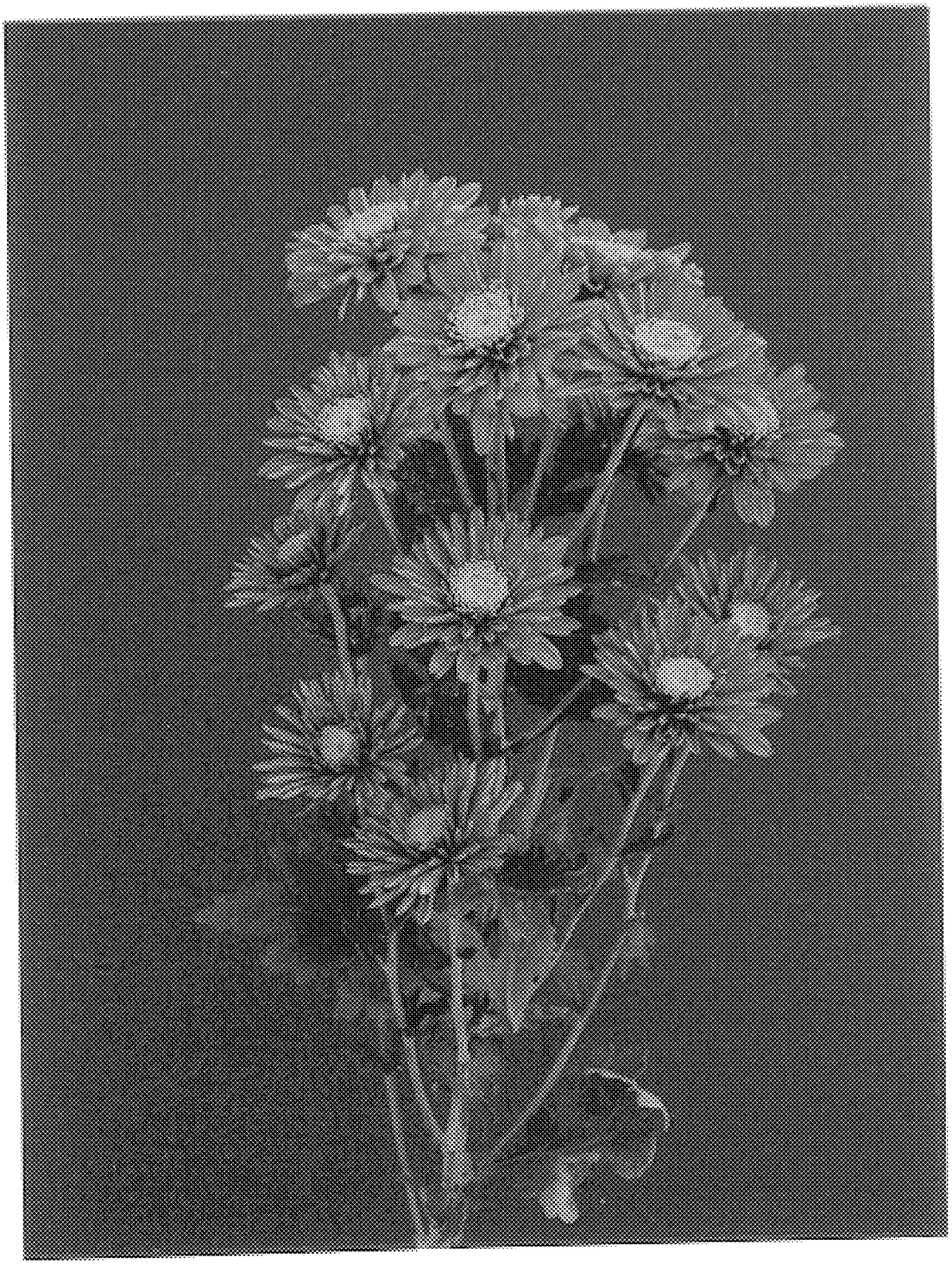

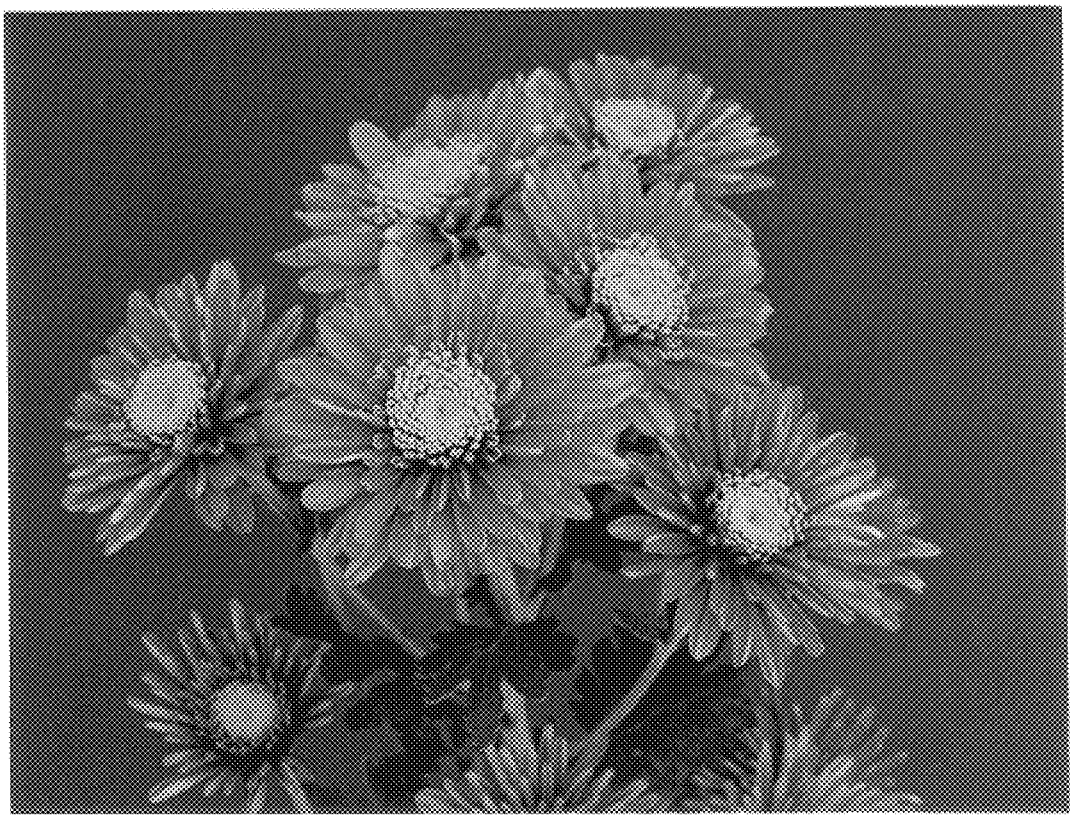

* * * * *